(12) United States Patent
Blank et al.

(10) Patent No.: US 7,534,350 B2
(45) Date of Patent: May 19, 2009

(54) LIQUID MEDIUM TREATMENT METHOD AND DEVICE

(76) Inventors: Pol Emanuilovich Blank, UL. 8 Marta. D. 15A. KV. 36, 125319 Moscow (RU); Emanuil Ihilovich Blank, UL. 8 Marta. D. 15A. KV. 36, 125319 Moscow (RU)

( * ) Notice: Subject to any disclaimer, the term of this patent is extended or adjusted under 35 U.S.C. 154(b) by 59 days.

(21) Appl. No.: 11/665,290

(22) PCT Filed: Dec. 29, 2004

(86) PCT No.: PCT/RU2004/000531

§ 371 (c)(1),
(2), (4) Date: Apr. 13, 2007

(87) PCT Pub. No.: WO2006/043850

PCT Pub. Date: Apr. 27, 2006

(65) Prior Publication Data

US 2007/0284304 A1  Dec. 13, 2007

(30) Foreign Application Priority Data

Oct. 15, 2004  (RU) .............................. 2004129950

(51) Int. Cl.
*C02F 3/32* (2006.01)
*C02F 1/68* (2006.01)
*A61K 35/02* (2006.01)

(52) U.S. Cl. ...................... 210/602; 210/620; 210/749; 210/758; 210/167.11; 210/220

(58) Field of Classification Search ................. 210/602, 210/620, 749, 758, 760, 167.21, 175, 220, 210/221.1, 221.2, 167.11

See application file for complete search history.

(56) References Cited

U.S. PATENT DOCUMENTS 4,253,949 A  3/1981  Hines et al.
5,512,084 A * 4/1996  Mauterer ..................... 95/199

FOREIGN PATENT DOCUMENTS

| JP | 3-56199 | * | 3/1991 |
| JP | 09-117784 A | | 5/1997 |
| RU | 2094394 C1 | | 10/1997 |
| RU | 2230996 C1 | | 6/2004 |
| SU | 997603 A3 | | 2/1983 |

OTHER PUBLICATIONS

Sun Min Kim et al., "Antioxidative Activity of Sulfur-containing Flavor Compounds in Garlic", Biosci, Biotech Biochem 1997, 1482-1485.
Ing. f. Landtechnik H.-H. Gahrns, "Technische Belüftung steigert Effektivität der Forrellenproduktion", Z. Binnenfischerei DDR, 1988, t.35, No. 6, pp. 209-214.
Schramm, et al., "Notes on Two Feed Types and Methods for Steelhead Trout Production", Program, Fish-Cuturist 1984, t. 46, No. 1, pp. 44-47.
Dr. F. Rümmler, "Erste Veruche zur $K_{1-2}$-Produktion in einer Anlage mit Sauerstoffbegasung und Rundbecken", Z. Binnenfischerei DDR, 1987, t.34, No. 6, pp. 179-185.
International Search Report of PCT/RU2004/000531, filed Dec. 24, 2004.

* cited by examiner

*Primary Examiner*—Fred Prince
(74) *Attorney, Agent, or Firm*—Collard & Roe, P.C.

(57) ABSTRACT

The invention relates to saturating various fluid media with oxygen, for example for aeration and can be used for the food industry, pharmaceutics, perfumery and cosmetics, physio- and aromotherapy, water supply systems, fishing and agriculture, including producing beverages, good additives, drugs, novel perfume and cosmetic products, inhalation and bathing, for improving the habitat and increasing a productivity of fish and other useful animals and microorganisms in aquariums, ponds, pools and for producing means for processing plants and animals. The inventive method for processing a fluid medium consists in passing an oxygen-containing gas flow which is pre-saturated by phyto-excretes of vegetating or cut plants through said medium. Said invention makes it possible to saturate fluid media with well-being improving, human-healthy, ecologically stable, useful for animal, beneficial insects, animalcular microorganisms and plants productivity, naturally reproducible ingredients, for example aeroions, aromatic oils and phytoncides which reduce the number of harmful bacteria and viruses.

15 Claims, 1 Drawing Sheet

LIQUID MEDIUM TREATMENT METHOD AND DEVICE

CROSS REFERENCE TO RELATED APPLICATIONS

Figure 1:
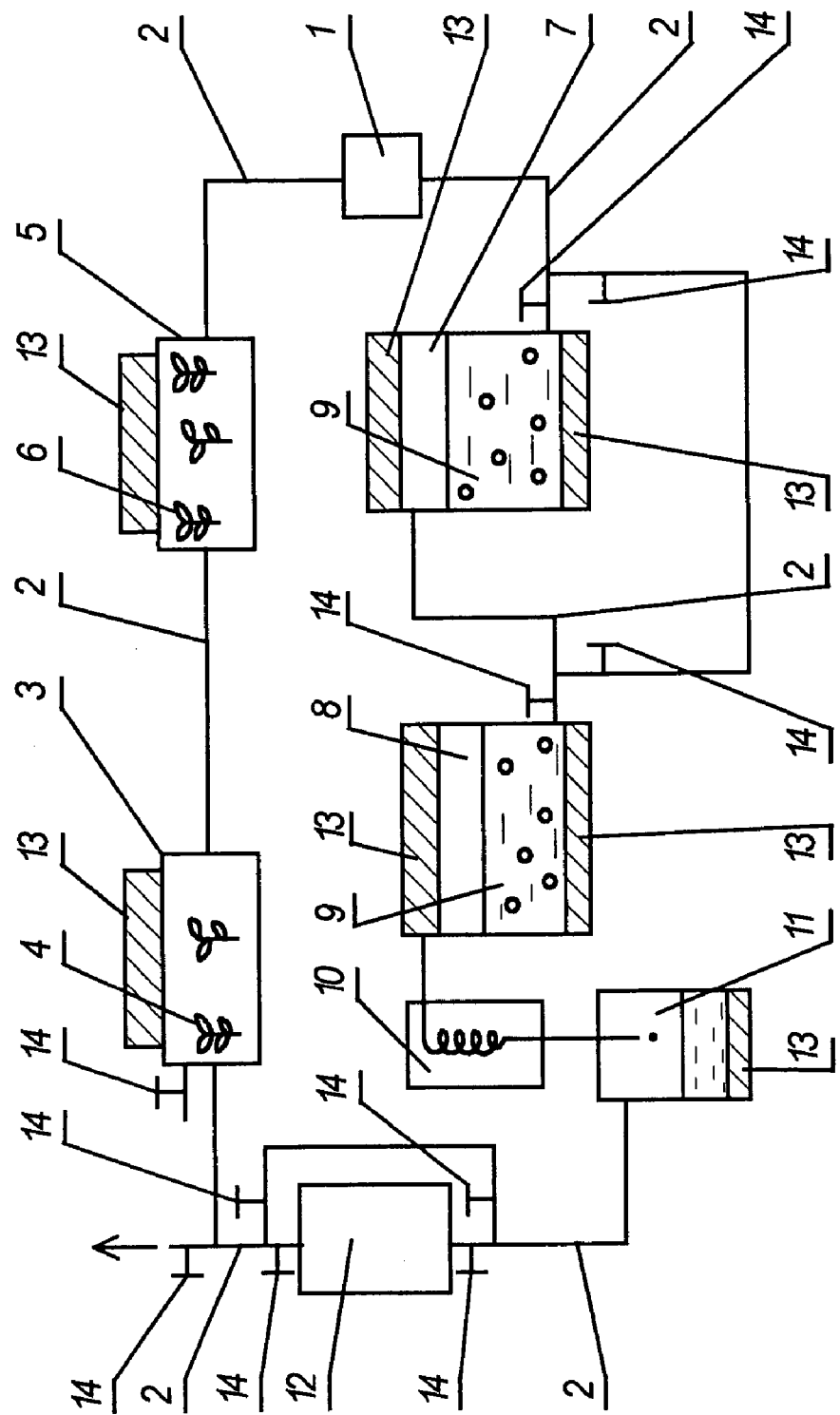

Applicants claim priority under 35 U.S.C. 119 of Russian Application No. 2004 129950 filed Oct. 15, 2004. Applicants also claim priority under 35 U.S.C. 365 of PCT/RU2004/000531 filed Dec, 29, 2004. The international application under PCT article 21(2) was not published in English.

FIELD OF THE INVENTION

The invention relates to saturating various fluid media with oxygen, for example for aeration and can be used for the food industry, pharmaceutics, perfumery and cosmetics, physio- and aromatherapy, water supply systems, fishing and agriculture, including producing beverages, food additives, drugs, novel perfume and cosmetic products, inhalation and bathing, for improving the habitat and increasing a productivity of fish and other beneficial animals and microorganisms in aquariums, ponds, pools and for producing means for treating plants and animals.

BACKGROUND OF THE INVENTION

Some methods and devices for changing the properties of water, fluids and other substances including the purification, supply, injection (pressure carbonation) or air and other gases passage through them stages are already known (Gahrns H.-H. Tehcniche Beluftung Steigert Effectivitat der Forellenproduktion (Use of Water Reservoir Aeration for Growing up Trouts) [1]; Z. Binnenfischerei DDR, 1988, t.35, No. 6, s. 209-214 [1]; Kindschi G. A. Notes on two feed types and methods for steelhead trout production [2]; Program. Fish-Cuturist, 1984, t.46, No. 1, p. 44-47 [2]; Rummler F., Pfeifer M. Erste Versuche zur K (1-2) -Produktion in einer Anlage mit Sauerstoffbegasung und Rundbecken. (First Experiments in Growing Up One- and Two-Year Old Carps in Oxygen-Rich Round Pools) Z. Binnenfischerei DDR, 1987, t. 34, No. 6, s. 179-185 [3]).

The disadvantage f these methods and devices is poor integrated effect caused by insufficient number of effective substances and nonrecoverable (non-renewable by natural way) use of some important components (for example, oxygen), filter fillers and materials and etc.).

DISCLOSURE OF THE INVENTION

The object of this invention is to eliminate the said disadvantages, to increase the content of oxygen in various liquid media, as well as saturation of liquid media with health-improving, salubrious, improving ecological stability and fertility of animals, useful insects, protozoal micro-organisms and plants, reducing all-up the number of deleterious bacteria and viruses, as well as their saturation, ingredients continuously renewable in a natural way, for example, air ions, aromatic oils, phytoncids.

Other additionally achievable objects may become clear from the invention disclosure.

The set task can be solved by that in the method of liquid medium treatment including passage of oxygen-containing gaseous media flow through it, the gaseous media is preliminarily saturated with phyto-egestas of vegetating or cut plants.

In particular implementations of the invention, the set task is solved as follows:
 the gaseous medium is saturated with phyto-egestas of plants by passing the flow of said medium through the chamber with the plants, evolving phyto-egestas;
 prior to its saturation with phyto-egestas of plants, the gaseous medium is purified of harmful admixtures by passing the flow of the said medium through the additional chamber with vegetating and/or cut plants, absorbing the respective harmful admixtures;
 plants are subjected to thermal, or luminous, or audio, or electromagnetic effect;
 liquid medium is subjected to thermal, or luminous, or audio, or electromagnetic effect;
 in the process of passing the gaseous medium flow, physical or chemical parameters of the gaseous medium are changed;
 treatment is performed in the presence of plant oily extracts;
 after passing the gaseous medium saturated with phyto-egestas through the liquid medium, a portion of gaseous liquid is taken with its subsequent condensation and collection of obtained concentrate of vegetational egestas;
 before the gaseous medium is passed through the liquid medium, it is accumulated under pressure in holding tanks for obtaining, for example, carbonated beverages.

The set task is also solved by the device for implementing the method, in compliance with which it contains the gaseous medium delivery means with delivery and suction branch pipes, at least one tank for liquid medium, at least one chamber with the plants evolving phyto-egestas, interconnected by the gas pipes, with the delivery branch pipe of the sad delivery means connected to the liquid medium tank through the gas pipes, and the suction branch pipe - connected with the chamber with plants.

In particular implementations of the invention, the set task is solved as follows:
 the device is equipped with a chamber with the plants, absorbing harmful admixtures and connected with the chamber accommodating the plants evolving phyto-egestas;
 the chambers for the plants and the tanks for fluid medium may be equipped with the appliances for controlling the water, gas, food and light modes, as well as for chemical, audio, light, electromagnetic and other treatment of plants;
 the device may contain additionally the appliances for condensation of egestas mounted at the liquid medium tank outlet for more complete collection of vegetational egestas;
 the chambers with plants may be of a toroidal shape.

The invention is based on the idea to saturate the liquid medium not only with oxygen but also with other beneficial substances—vegetational egestas.

During the experiments, it was found out rather unexpectedly that the saturated medium not only acquires the beneficial properties inherent to vegetational egestas, but the content of oxygen also increased in it.

Phyto-egestas are essentially the metabolism final products evolved outside by the plant. Special glandules of plants participate in egestion, and the cellular surface, as well, and the egestion process runs by passive wash off by precipitation and mainly—by evaporation.

The prevailing phyto-egestas mainly include terpenoids.

Terpenoids are essentially natural hydrocarbons composed of $C_{10}H_{16}$ and their multiple oxygenous derivates (alcohols, aldehydes, ketones, acids, oxides and etc.). They are contained mainly in essential oils of flowers, leaves, fir-needles, plant fruits, in various natural resins (balsams) of coniferous trees (pines, firs, cedars, fir trees and etc.).

Terpenoids differ from other organic compounds of the same composition in their tendency to isomeration, cyclization and polymerization which often run even under very soft conditions (low temperature, dilution and etc.).

This large class of natural compounds includes monoterpenes ($C_{10}H_{16}$), sesquiterpenes ($C_{15}H_{24}$), diterpenes ($C_{20}H_{32}$), triterpenes ($C_{30}H_{48}$), tetraterpenes ($C_{40}H_{64}$) and polyterpenes ($C_{10}H_{16}$). These multiple groups of substances have practically been found in all tissues and medicinal plants. They are contained in essential oils (contain monoterpenes and sesquiterpenes), in amarines (mainly, sesquiterpenuic lactones); resins and balsams (contain diterpenes).

The terpenic compounds are active participants in the metabolic processes, running in the vegetational organism which is testified by their high reactivity. Some terpenoids regulate activity of plant genes and possess a chromatophore system, may absorb radiant energy, participate in photochemical reactions. The carbon chains of individual terpenoids are the key intermediate products on the way of biosynthesis of such biologically active substances as steroid hormones, enzymes, antioxidants, vitamins D, E, K, bile acids.

The terpenic compounds evolved from the plants have a wide range of biological effects found out in them and generally they are low-toxic and single specific action is extrinsic to them—the potential of their biological effect is distributed evenly among various systems and organs.

Associated with terpenic compounds is phytoncidic activity of essential oils of many plants of a natural flora of various regions of the world. Many of these substances produce a harmful effect on diverse gram-positive and gram-negative microflora, some species of mushrooms, animalculara and viruses.

That is why currently against the background of the increased antibiotic resistance of germs of purulent infections and dominating relevancy of the opportunistic microflora, use of natural terpenoids becomes especially important.

The liquid medium is essentially any liquid medium: water and water environments, for example, for production of fishes, aqueous or hydroalcoholic solutions, liquid cosmetics in the form of lotions or creams (emulsions), beverages and etc.

The oxygenated gaseous medium in accordance with this invention is essentially any gaseous medium, for example, air, industrially supplied oxygen or any gas mixture with oxygen, carbon dioxide, as well as the substances in the gaseous state, for example, water vapor, which may be used for saturation of liquid medium (ref. above) with oxygen.

The oxygenated gaseous medium most intensively saturated with phyto-egestas may be obtained by arranging the cut or vegetating plants in the closed chamber and take egestas from this chamber. To intensify useful effects, including the psychological ones, cut and dried plants, for example nosegays, may be placed in the chamber and used.

The egestas may be taken both by pumping the oxygenated medium through this closed chamber and by scavenging the gaseous medium existing in the chamber.

To obtain more pure oxygenated gaseous medium, it would be better to purify it by passing the flow of the said medium through the additional chamber with the plants absorbing the respective harmful impurities. For example, for medium purification, it would be good to use the following plants for removing the following substances:

For removing benzene (source material for many types of synthetic resin, carcinogen)—*Aglaonema, Chlorophytum, Chrysanthemums, dragon-tree, Epipremnum, Gerbera, Sansevieria, Spatiphillum*;

For removing trichloroethylene (colorless fluid with a chloroform smell, contained in varnish and adhesive, carcinogen)—*Chamaedorea, Chrysanthemums, dragon-tree, Epipremnum, ficus benjamina, Gerbera, ivy, Sansevieria, Spatiphillum;*

For removing formaldehyde (source material for artificial resins, glue base for mounting plates, carcinogen)—sword fern (*Nephrolepis*), *Marguerite, dragon-tree, Chamaedorea, ficus benjamina, ivy, Spathiphyllum, Schefflera,* tuftroot (*Dieffenbachia*);

For removing xylene and toluene (used in polymeric coating)—tuftroot (*Dieffenbachia*), sword fern (*Nephrolepis*), *Anthurium, ficus benjamina;*

For removing ammonia (carcinogenic component of multiple nitrogen-containing industrial substances)—*Anthurium , Chrysanthemum frutescens, arrowroot, ficus benjamina, dragon-tree, azalea.*

For controlling the composition and amount of the substances absorbed and evolved by plants, an additional effect may be produced both on the liquid and gaseous medium and on plants. The effect may be produced by heat, electromagnetic radiation, light or sound.

Particularly, plants are exposed to heat, light, sound or electromagnetic radiation or to their combinations. In the device involved in implementation of this invention, special appliances are provided for controlling the water, gas, food, light modes, as well as for chemical, audio, luminous, electromagnetic and any other treatment of plants.

The liquid medium can also be subjected to additional effect—thermal, luminous, audio or electromagnetic, which also makes it possible to increase the amount of dissolved vegetational egestas.

For this purpose, in the process of passage of the gaseous medium flow, the gaseous medium physical and chemical parameters may be changed (pumping rate, chemical composition of the medium, for example, content of oxygen in it, temperature and humidity).

In some particular implementations of the invention, to increase the useful effect, treatment is performed in the presence of plant oily extracts.

In other implementations of the invention, for more complete use, as well as for collection of beneficial substances contained in the vegetational egestas, after the gaseous medium saturated with phyto-egestas is passed through the liquid medium, a part the gaseous medium is taken with its subsequent condensation and collection of obtained vegetational egestas.

Sometimes, it is convenient not to use the gaseous medium saturated with phyto-egestas immediately. In this event, the gaseous medium saturated with phyto-egestas, prior to its passage through the liquid medium is accumulated under pressure in accumulation tanks for use in further production, for example, of carbonated beverages.

The invention may find the widest application, for example, if the air mixture after the saturation chamber is directed to the reservoir shaped as a pool, Jacuzzi or bath for patients, a considerable health-improving effect may be achieved with the vegetational egestas affecting through the skin surface and then (after blow out of the bubbles on the liquid surface) also through respiratory organs.

Another aspect of invention application may be water aeration (natural or artificial process of water enrichment with air oxygen) employed for:

increasing concentration of dissolved oxygen;

removing of smell producing gases and substances from water;

water deferrization;

wastewater biological purification;

use in aquariums and for industrial fish farming.

LIST OF DRAWINGS

FIG. 1 shows the device general view.

PREFERRED EMBODIMENT OF INVENTION

The liquid medium treatment device is designed as follows.

The vacuum compressor pump 1 is connected with the aid of gas pipes 2 with chambers 3 for group of plants 4 absorbing harmful substances from oxygenated gaseous medium and chambers 5 filled with plants 6 saturating air with egestas (terpenoids), as well as with tanks 7 and 8 for saturation of liquid medium (water, fluids and other liquid substances) 9 with phyto-egestas, and with appliances 10 and 11 for collection (condensation) and accumulation of 12 useful ingredients. In this case, chambers 3 and 5 for plants and tanks 1 and 8 are equipped with appliances 13 for controlling temperature, light and other modes, as well as the shutoff cocks and other fittings 14.

First the oxygenated gaseous medium is supplied to chamber 3 filled with vegetating (intact) plants 4 absorbing harmful substances (benzenes, phenols, carbon monoxide and etc) from air, then, through the air pipes 2 air mixture is supplied into chamber 5, filled with vegetating (intact) or specially prepared (for example, cut) plants 6, where it is saturated with phyto-egestas. After this, using compressor 1 air mixture is supplied into tanks 7 and 8 where it is passed under different pressure through water, fluids and/or other substances and thus they are saturated with the said beneficial phyto-egestas which are also collected with the aid of condensers (coolers) 10 and accumulated in special tanks under pressure 11 for subsequent use.

EXAMPLE 1

In compliance with all described above, an air flow which has passed through the chambers with the myrtle plants (*Myrtus communis L.*) was passed through the water tank.

The time of treatment was from 1 to 6 hours.

In so doing, all given examples showed that as a result of passing the air saturated in the device with phyto-egestas through the water with initial oxygen content of 7.1 mg/lit, the oxygen content in it increases (ref. Table 1).

In this case, the amount of volatile terpenoids (essential oils) in the air flow increased from I mg per cubic meter after pumping air for one hour at a rate of 0.2 lit/s via the chamber with the plants through the closed circuit to 4 mg/m$^3$ for 6 hours, and their content in water (with water temperature of +25° C.) through which this air was passed—from 0.001 to 0.003 mg/lit (at an air temperature of +25° C. and with water amount of 1 lit). At the pumped air temperature of +35° C. the amount of volatile terpenoids in the air increased to 1.5 mg/m$^3$ after 1 hour of pumping at a rate of 0.2 lit/s via the chamber with plants through the closed-loop circuit to 6 mg/m$^3$ for 6 hours, and their content in water (with the average water temperature of +27° C.)—to 0.008 (after 1 hour of pumping) and 0.029 mg/lit (after 6 hours of pumping).

So, heating of the air to be pumped and during pumping makes it possible to increase both the amount terpenoids (essential oils) emitted by plants and the degree of saturation of water with them through which air saturated with phyto-egestas is passed.

EXAMPLE 2

In compliance with all said above, the flow of air passed through the chambers with the lavender plants was passed through the tanks containing various fluids.

Additionally, the plants were illuminated with light.

Table 2 contains the data showing influence of plants additional illumination in the saturation chamber on the oxygen content in water, mouthwash and in cosmetic cream (the initial oxygen content in them is 8.7 mg/lit, 6.1 mg/lit, 2.8 mg/lit, respectively) as a result of passing air with phyto-egestas through them.

So, illumination of plants in saturation chambers may be used for controlling oxygen content in water, fluids and other substances being treated.

EXAMPLE 3

In compliance with all said above, the flow of air passed through the chambers with lavender plants was passed through the tank with water.

Table 3 contains the data showing influence of air flow passed through the lavender plants in the saturation chamber on the content of oxygen and terpenoids in water with initial content of 8.1 mg/lit after 1 hour of treatment with air containing phyto-egestas.

So, increase of the rate of flow of the air pumped through the chambers with the plants and water tanks increases considerably saturation of water with oxygen and terpenoids (essential oils).

Additional treatment of water containing phyto-egestas with ultrasound (while passing the gaseous mixture with phyto-egestas through water arranged in laboratory ultrasonic dispersant at a rate of 1 lit/s) increases the content of oxygen in water for 1 hour from 12.4 to 14.0 mg/lit, terpenoids—from 0.019 to 0.042 mg/lit.

The increase of the amount of oxygen in water, fluid or any other substance makes them not only of higher quality for human use, but also promotes to considerable increase of fish fertility ([1]; [2]; [3]; Skipetrov V. P. Air Ions and Life. Saransk, Krasny Oktyabr printery, 1997).

EXAMPLE 4

The influence of time of passing air saturated with phyto-egestas through water on the population of *collibacillus* was studied. For this purpose, the air flow was passed through the chambers with various plants. The data are given in Table 4.

So, phytoncids contained in phyto-egestas reduce considerably the number of pathogenic germs and improve quality of water.

Some publications (Grodzinsky A. M. Phytodesign and Phytoncids.—K.: Naukova Dumka. 1973; Grodzinsky A. M. Experimental Allelopathy.—Naukova Dumka. 1987; Sun Min Kim, Kikue Kubota, and Akio Kobayashi. Antioxidative Activity of Sulfur-containing Flavor Compounds in Garlic.

Biosci. Biotech. Biochem., 61 (9), 1482-1485, 1997) show efficient effect of phytoncids on destructive insects and etc.

EXAMPLE 5

Table 5 contains the data showing the influence of gaseous mixture temperature in phyto-chambers and depth of its subsequent cooling on the amount of collected condensate of phyto-egestas.

The table shows that the amount of condensate of phyto-egestas increases as the temperature of gaseous medium in phyto-chambers rises and the cooling temperature in the condensation chambers drops.

EXAMPLE 6

Table 6 contains the data showing the influence of temperature and intensity of illumination of lavender plants on the amount and type of evolved phyto-egestas. The $1^{st}$ method was used for determining the amount of condensate in the collecting tank after the +40° C. gas mixture with phyto-egestas cooling after the alcohol cooling chamber. Under the second method, on its way to the phyto-chamber, the gas mixture was purified with the aid of special filter with absorbents (dried calcium chloride and activated carbon) to remove vapors of water and other substances. Similar filter was mounted at the phyto-chamber outlet. It was weighed before and 1 hour after passage of gas mixture with phyto-egestas through it. The difference in masses testified to the total amount of phyto-egestas. The amount of essential oils and other organic substances was determined with the aid of organic solvents and gas chromatography.

So, variation of the illumination intensity in the phyto-chamber may be used for controlling the amount of water, essential oils and other organic substances collectable as a result of absorption or condensation.

EXAMPLE 7

Table 7 contains the data showing the influence of biologically active substance—tomatozide (E. I. Blank, A. G Jacote et al. Method of White Beet Seeds Pretreatment. USSR author's certificate No. 993845, 1980) dissolved in spraydown water on the amount of oxygen and terpenoids dissolved in water with initial oxygen content of 7.9 mg/lit with lavender phyto-egestas passed through it for one hour. The experiment was held 24 hours after moistening soil with the said tomatozide solution in the pot with the growing lavender.

So, treatment of plants with biologically active substances may control the phyto-egestas evolving process.

Use of gaseous excreta of live (vegetating) or ground plants for treatment of water (drinking, for baths, pools), alcoholic and nonalcoholic beverages, food additives, dosage forms, fluids (perfume, lotions, mouthwashes), other substances (creams, muds) and etc. results in considerable increase of content of oxygen, phytoncids, natural aromatic components with useful negative air ions, pure transpiration (evolved by plants) water, biologically active pheromones and etc. in them.

Table 8 contains the data showing content of oxygen and terpenoids in water after one-hour passage of air through it containing phyto-egestas of lavender plants previously subjected to five-minute microwave treatment.

So, electromagnetic treatment of plants may control the phyto-egestas evolved by them.

Table 9 contains the data showing content of oxygen and terpenoids in water in case of its 60-second microwave treatment every 10 minutes during 60-minute passage of air mixture with phyto-egestas of lavender plants through it.

So, the electromagnetic treatment of liquid medium with electromagnetic field during passage of air mixture with phyto-egestas of plants through it may control the amount of phyto-egestas adsorbed in this liquid medium.

Table 10 contains the data showing content of oxygen and terpenoids in water and orange juice at different temperatures and PH after passage of lavender phyto-egestas through them.

So, control of the liquid medium PH, its temperature and composition may control the amount of phyto-egestas adsorbed by this liquid medium during passage of gas mixture with phyto-egestas of plants through it.

TABLE 1

| | Content of oxygen in water of 20° C. temperature, mg/lit | |
|---|---|---|
| Treatment time, h | with water treated with air (test) | with water treated with air saturated with myrtle egestas |
| 1 | 7.5 | 9.1 |
| 2 | 8.4 | 9.4 |
| 6 | 8.7 | 9.8 |

Note:
Differences are essential under the 1$^{st}$ Student criterion (95-% level of relevancy).

TABLE 2

| Passage of air with phyto-egestas during | Content of oxygen during additional illumination, mg/lit | | |
|---|---|---|---|
| 1 hour through: | 100 W/m$^2$ | 300 W/m$^2$ | 500 W/m$^2$ |
| Water | 9.9 | 11.1 | 10.8 |
| Mouthwash | 8.4 | 9.6 | 9.0 |
| Liquid cream | 7.8 | 8.7 | 8.4 |

Note:
Differences are essential under the 1$^{st}$ Student criterion (95-% level of relevancy).

TABLE 3

| | Content in water of, mg/lit | |
|---|---|---|
| Rate of air flow, lit/s | oxygen | terpenoids |
| 0.2 | 9.1 | 0.002 |
| 0.5 | 10.5 | 0.011 |
| 1.0 | 12.4 | 0.019 |

TABLE 4

| | Collie index | | | |
|---|---|---|---|---|
| Types of plants in saturation chambers | Original amount of *bacterium coli* | in 1 hour | in 2 hours | in 6 hours |
| Myrtle (*Myrtus communis L.*) | 65 | 40 | 34 | 29 |
| Garlic (*Allium sativum L.*) | 65 | 28 | 11 | 2 |

TABLE 4-continued

|  | Collie index | | | |
| --- | --- | --- | --- | --- |
| Types of plants in saturation chambers | Original amount of bacterium coli | in 1 hour | in 2 hours | in 6 hours |
| Garlic (*Allium sativum L.*) immediately after grinding | 65 | 17 | 11 | 8 |

Note:
Differences are essential under the 1$^{st}$ Student criterion (95-% level of relevancy).

TABLE 5

|  | Amount of collected condensate (less fluid condensed from gas mixture w/o phyto-egestas - test) in terms of 1 dm$^2$ of leaf surface, g/h T of gas mixture | | | |
| --- | --- | --- | --- | --- |
| Types of plants in saturation chambers | 25° C. w.c.* | 40° C. w.c.* | 25° C. a.c.* | 40° C. a.c.* |
| Myrtle (*Myrtus communis L.*) | 1.1 | 4.9 | 4.4 | 9.2 |
| Garlic (*Allium sativum L.*) | 1.6 | 5.3 | 5.2 | 12.9 |
| Lavender | 1.9 | 7.6 | 6.8 | 15.1 |

*w.c. - condensation was performed by cooling the gas mixture with phyto-egestas in water cooler with running water of 17° C. temperature;
a.c. - condensation was performed with the aid of cooled ethyl alcohol of −15° C. temperature (the gas mixture with phyto-egestas is passed through the pipe coil flown with running water or dipped in 96-% ethyl alcohol filled in a freezing chamber).
Note:
Differences are essential under the 1st Student criterion (95-% level of relevancy).

TABLE 6

| Method of determining the amount and type of phyto-egestas | Illumination intensity in phyto-chamber 300 $W/m^2$: Amount phyto-egestas, $g/dm^2$ | Essential oils, % | W/o illumination: Amount of phyto-egestas, $g/dm^2$ | Essential oils, % |
|---|---|---|---|---|
| 1. Condensation with alcohol cooling −15° C. | 15.2 | 0.78 | 18.7 | 1.58 |
| 2. Weighing of filter with absorbents | 17.1 | 0.95 | 19.6 | 2.4 |

TABLE 7

| Version | Content of in water, mg/lit: oxygen | terpenoids |
|---|---|---|
| Test (watering) | 9.4 | 0.019 |
| Sprinkling with 0.001% tomatozide | 14.1 | 0.024 |
| Test w/o watering | 8.5 | 0.017 |

TABLE 8

| Microwave treatment power, W | Content of, mg/lit: oxygen | terpenoids |
|---|---|---|
| 0 | 9.1 | 0.020 |
| 100 | 9.1 | 0.031 |
| 180 | 8.5 | 0.038 |

TABLE 9

| Microwave treatment power, W | Content of, mg/lit: oxygen | terpenoids |
|---|---|---|
| 0 | 9.1 | 0.020 |
| 100 | 9.0 | 0.026 |
| 180 | 8.8 | 0.020 |

TABLE 10

| PH of fluids | Content of, mg/lit: oxygen in water 18° C. | oxygen in orange juice 18° C. | oxygen in orange juice 10° C. | terpenoids in water 18° C. | terpenoids in orange juice 18° C. | terpenoids in orange juice 10° C. |
|---|---|---|---|---|---|---|
| 7.0 | 9.1 | | | 0.020 | | |
| 6.0 | 9.0 | | | 0.026 | | |
| 4.0 | | 15.7 | 18.3 | | 0.028 | 0.041 |
| 3.0 | | 14.3 | 16.1 | | 0.033 | 0.047 |

The invention claimed is:

1. A method of liquid medium treatment including passage of oxygenated gaseous medium flow through liquid medium wherein the gaseous medium is previously saturated with phyto-egestas of vegetating or cut plants.

2. The method according to claim 1, wherein gaseous medium is saturated with plant phyto-egestas by passage of the flow of the said medium through a first chamber with plants, evolving phyto-egestas.

3. The method according to claim 2, wherein prior to saturation of the gaseous medium with plant phyto-egestas, the gaseous medium is purified of harmful admixtures by passing the flow of the said medium through a second chamber with vegetating and/or cut plants absorbing the harmful admixtures.

4. The method according to claim 1, wherein plants are exposed to heat, or light, or sound or electromagnetic field.

5. The method according to claim 1, wherein the liquid medium is exposed to heat, or light, or sound or electromagnetic field.

6. The method according to claim 1, wherein in the passage of oxygenated gaseous medium flow through the liquid medium, physical or chemical parameters are varied.

7. The method according to claim 1 wherein treatment is performed in the presence of plant oily extracts.

8. The method according to claim 1, wherein after passage of gaseous medium saturated with phyto-egestas through the liquid medium, some portion of the gaseous medium is taken with condensate of vegetational egestas obtained from subsequent condensation and collection of the gaseous medium.

9. The method according to claim 1, wherein prior passage through the liquid medium the saturated gaseous medium is accumulated under pressure in accumulation tanks for obtaining carbonated beverages.

10. The A device for liquid medium treatment containing at least one appliance for gaseous medium delivery having delivery and suction branch pipes, at least one tank for liquid medium, at least one chamber containing plants evolving phyto-egestas with the delivery branch pipe of the at least one appliance connected to the liquid medium tank and the suction branch pipe to the chamber with the plants evolving phyto-egestas.

11. The device according to claim 10, comprising at least one respective chamber with the plants absorbing impurities and connected to the chamber with the plants evolving phyto-egestas.

12. The device according to claim 10, wherein the at least one appliance comprises a plurality of appliances, the at least one chamber comprises a plurality of chambers and the at least one tank comprises a plurality of tanks equipped with the appliances for controlling at least one of the modes: water, gas, food, light, and for at least one type of plants treatment: chemical, audio, light and electromagnetic.

13. The device according to claim 10, further comprising appliances for condensation of egestas mounted at an outlet of the tank with liquid medium.

14. The device according to claim 10, wherein the at least one chamber comprises a plurality of chambers having a toroidal shape.

15. The device according to claim 10, wherein the at least one tank is made in the form of a bath or a pool.

* * * * *

UNITED STATES PATENT AND TRADEMARK OFFICE
CERTIFICATE OF CORRECTION

| | |
|---|---|
| PATENT NO. | : 7,534,350 B2 |
| APPLICATION NO. | : 11/665290 |
| DATED | : May 19, 2009 |
| INVENTOR(S) | : Blank et al. |

Page 1 of 1

It is certified that error appears in the above-identified patent and that said Letters Patent is hereby corrected as shown below:

In Column 10, line 39, (Line 2 of Claim 1) after the word "through" please add: --a--.

In Column 11, line 1 (Line 1 of Claim 9) after the word "prior" please add: --to--.

Signed and Sealed this

Twenty-fifth Day of August, 2009

David J. Kappos
*Director of the United States Patent and Trademark Office*